US010463332B2

(12) United States Patent
Rowley Grant et al.

(10) Patent No.: US 10,463,332 B2
(45) Date of Patent: Nov. 5, 2019

(54) SPECTRAL TOPOGRAM-BASED DETERMINATION OF IMAGING PARAMETERS

(71) Applicant: Siemens Healthcare GmbH, Erlangen (DE)

(72) Inventors: Katharine Lynn Rowley Grant, Rochester, MN (US); Bernhard Schmidt, Fueth (DE)

(73) Assignee: Siemens Healthcare GmbH, Erlangen (DE)

( * ) Notice: Subject to any disclaimer, the term of this patent is extended or adjusted under 35 U.S.C. 154(b) by 106 days.

(21) Appl. No.: 15/887,288

(22) Filed: Feb. 2, 2018

(65) Prior Publication Data
US 2019/0239839 A1    Aug. 8, 2019

(51) Int. Cl.
*A61B 6/00*    (2006.01)
*G01N 23/04*    (2018.01)
*G01N 23/046*    (2018.01)

(52) U.S. Cl.
CPC ............ *A61B 6/488* (2013.01); *A61B 6/5217* (2013.01); *A61B 6/544* (2013.01); *G01N 23/046* (2013.01); *G01N 2223/1016* (2013.01); *G01N 2223/419* (2013.01)

(58) Field of Classification Search
CPC ....... A61B 6/488; A61B 6/5217; A61B 6/544; G01N 2223/1016; G01N 2223/419; G01N 23/046
See application file for complete search history.

(56) References Cited

U.S. PATENT DOCUMENTS

| | | | |
|---|---|---|---|
| 10,335,095 B2* | 7/2019 | Flohr | A61B 6/032 |
| 2014/0086383 A1* | 3/2014 | Huwer | A61B 6/505 |
| | | | 378/5 |
| 2016/0262713 A1* | 9/2016 | Flohr | A61B 6/5205 |
| 2016/0302751 A1* | 10/2016 | Grant | A61B 6/5205 |

OTHER PUBLICATIONS

Rego, Shawna L. et al. "CARE Dose4D CT Automatic Exposure Control System: Physics Principles an Practical Hints", Radiological Society of North America 2007 Scientific Assembly and Annual Meeting, Nov. 25-Nov. 30, 2007, Chicago, IL, 1pg.
Grant, Katharine et al. "CARE kV Automated Dose-Optimized Selection of X-ray Tube Voltage", White Paper, Siemens, 2011, Order No. A9115-11314-C1-4A00, pp: 1-8, 8 total pages.
Weir, Avril "The effect of topogram orientation on dose and image quality", Seventeenth meeting of the CT Users Group, Dec. 15, 2015, Oxfordshire, England, 16pgs.

* cited by examiner

*Primary Examiner* — Mark R Gaworecki

(57) ABSTRACT

A system includes acquisition of a spectral topogram of a target, determination, based on the spectral topogram, of an attenuation associated with each of a plurality of regions of the target and a composition of each of the plurality of regions, determination of imaging parameters associated with the plurality of regions based on the determined attenuation and composition, and acquisition of an image of the target based on the imaging parameters.

20 Claims, 5 Drawing Sheets

SPECTRAL TOPOGRAM-BASED DETERMINATION OF IMAGING PARAMETERS

BACKGROUND

X-ray images are commonly used to facilitate medical diagnosis and/or treatment. An X-ray image may be acquired by emitting radiation from an X-ray radiation source toward a patient and by receiving a radiation field of X-ray radiation which emerges from a side of the patient opposite the radiation source. The radiation intensity at a particular location of the received radiation field represents the attenuative properties of internal patient structures which lie along a divergent line between the radiation source and the particular location of the radiation field. The radiation intensities of the radiation field therefore represent a two-dimensional projection image of these structures.

The benefits of X-ray imaging should be balanced against the radiation dose received by a patient during imaging. This balance is particularly delicate in the case of computed tomography (CT) imaging, which reconstructs a three-dimensional CT image of the patient based on many X-ray projection images. The X-ray projection images are acquired from various projection angles, and each acquisition delivers a corresponding radiation dose to the patient.

The radiation dose delivered to a patient during CT imaging may be reduced by adjusting the radiation tube current based on the size and shape of the patient. For example, a larger patient may be imaged using a larger tube current than the tube current used to image a smaller patient. Other parameters imaging such as tube voltage may also be adjusted, based, for example, on whether the CT image includes injected contrast agent. Systems are desired to further reduce the radiation dose delivered to a patient while achieving suitable image quality.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments. Various modifications, however, will be readily apparent to those in the art.

Briefly, some embodiments operate to determine the composition of materials within a volume such as a patient body, and to determine parameters for subsequent imaging of the volume based on the determined composition. The determination of imaging parameters may also be based on attenuative properties of the volume, a type of imaging to be performed, and/or other factors. The imaging parameters may comprise one or more of an X-ray tube current, an X-ray tube voltage, a radiation dose, and other parameters.

Figure 1:
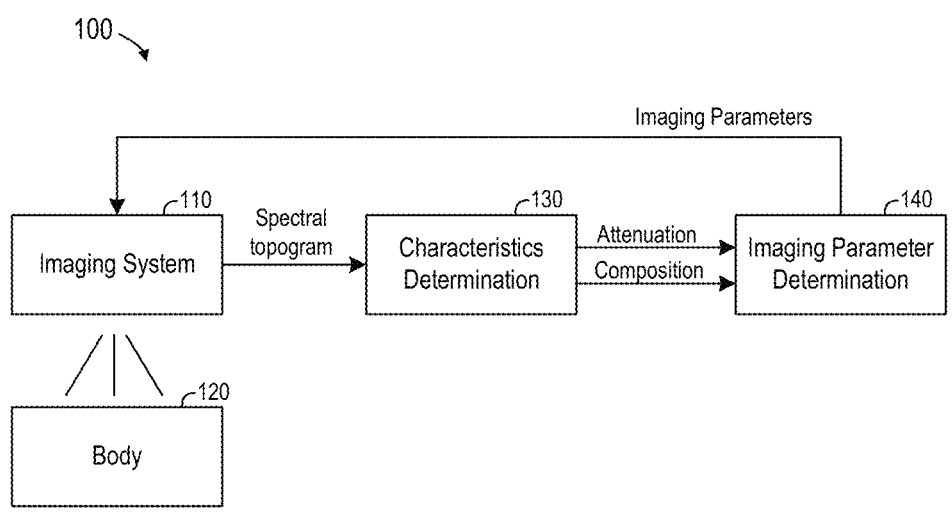
FIG. 1 is a block diagram of a system according to some embodiments.

FIG. 1 is a block diagram of system 100 according to some embodiments. Embodiments are not limited to the components and foregoing description of system 100. Each component of FIG. 1 may be implemented using one or more suitable devices, including a general-purpose device such as a programmable computer.

Imaging system 110 may comprise a CT imaging system as is known in the art. Imaging system 110 may emit X-ray radiation toward body 120 to acquire a topogram of body 120. In this regard, imaging system 110 includes a suitable radiation detector as is known in the art. According to some embodiments, the acquired topogram also includes spectral information. Generally, the spectral information provides an estimation of attenuation as a function of photon energy for each region of the topogram.

The spectral topogram is provided to characteristics determination component 130 of system 100 according to some embodiments. Characteristics determination component 130 determines various characteristics of body 120 based on the spectral topogram. The characteristics may include the attenuation exhibited by body 120 at various patient z-positions and from various projection angles, as well as the composition of different regions of body 120.

Imaging parameter determination component 140 determines imaging parameters to be used in a subsequent CT scan of body 120 based on the determined characteristics. The imaging parameters may be determined so as to achieve a desired image quality while limiting the radiation dose received by body 120 during the CT scan. For example, the tube current determined to acquire a projection image of a body region at a projection angle may be directly related to the attenuation of the body region at the projection angle, and inversely related to a contrast level associated with the composition of the body region (e.g., fat=high contrast level).

Figure 2:
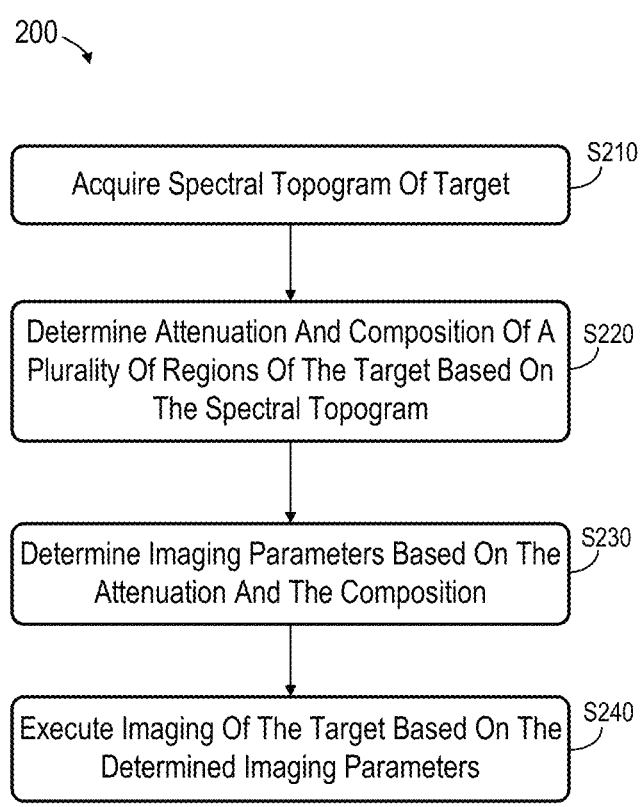
FIG. 2 comprises a flow diagram of a process according to some embodiments.

FIG. 2 comprises a flow diagram of process 200 according to some embodiments. Process 200 and the other processes described herein may be performed using any suitable combination of hardware, software or manual means. In some embodiments, one or more processing units (e.g., processors, processor cores, processor threads) execute program code to cause a computing system to perform one or more aspects of process 200. Such program code may be stored by any non-transitory tangible medium, including a fixed disk, a floppy disk, a CD, a DVD, a Flash drive, or a magnetic tape. Examples of process 200 will be described below with respect to the elements of system 100, but embodiments are not limited thereto.

Initially, a spectral topogram of a target is acquired at S210. A topogram may comprise a projection image used to localize the start location and end location of an imaging scan. Accordingly, the topogram need not exhibit high image quality and may therefore be acquired using a low radiation dose. In some embodiments, the topogram is acquired from one projection angle, and a corresponding projection from a perpendicular projection angle is estimated using a mathematical model as is known in the art. A rough three-dimensional topogram of the target may be reconstructed from the two projections in some embodiments using known techniques. Acquisition of a topogram at S210 may comprise operating an imaging system such as imaging system 110 to acquire a topogram of body 120 or acquiring topogram data of a target which was previously-acquired by an imaging system.

According to some embodiments, the acquired topogram also includes spectral information. Generally, the spectral information provides an estimation of attenuation as a function of photon energy for each region of the topogram. In one example, the spectral information indicates, for each region of the topogram, an attenuation determined in response to photons of a first energy level and an attenuation determined in response to photons of a second energy level. The spectral information may specify additional energy levels and corresponding attenuations for each region.

The spectral information may be determined by acquiring a first topogram using a single X-ray tube operating at a first voltage and then acquiring a second topogram using the same X-ray tube operating at a second voltage. In some embodiments, two topograms are acquired substantially concurrently using two X-ray tubes operating at different voltages and corresponding radiation detectors disposed opposite from the X-ray tubes. Some embodiments may utilize a photon counting detector, in which only one X-ray spectrum is emitted (e.g., from a single X-ray tube) and the detector thresholds received photons of the spectrum into different energy categories after they have passed thru body 120, thereby capturing the attenuation experienced by photons of different energy levels at each pixel of the detector. Embodiments are not limited to the above systems for acquiring a spectral topogram.

Next, at S220, attenuation and composition of regions of the target are determined based on the spectral topogram. The attenuations at various patient z-positions and from various projection angles may be determined from the spectral topogram based on the Hounsfield units associated with various regions within the topogram, without requiring the spectral information of the spectral topogram.

The Hounsfield units do not indicate the composition of each region, because different individual materials and combinations of multiple materials may exhibit a same attenuation for a given photon energy. As described above, the spectral information of the spectral topogram provides an estimation of attenuation as a function of photon energy for each region of the topogram. Notably, different materials behave according to different functions. For example, although iodine and calcium exhibit similar X-ray attenuations at high energy levels (e.g., 150 keV), iodine demonstrates a larger and known increase in X-ray attenuation versus calcium at lower energy levels. Accordingly, the composition of a region (i.e., the materials and concentrations of each material making up the region) may be determined at S220 based on the relationship between attenuation and photon energy which the spectral information associates with the region.

Imaging parameters to be used in a subsequent CT scan of the target are determined at S230 based on the determined attenuation and composition. With reference to system 100, the attenuation determined by characteristics determination component 130 may specify variations in X-ray attenuation depending on the projection angle, particularly in elliptical regions of body 120 such as the thorax and pelvis. If a constant tube current is used, the noise level in a reconstructed image is primarily determined by the X-ray projections through the most-attenuating projection angles. The X-ray projections through less-attenuating angles would therefore deliver radiation which increases the overall radiation dose received by the patient but does not improve the quality of the reconstructed image. Imaging parameter determination component 140 may therefore determine a tube current for each projection of the subsequent CT scan based upon the attenuation exhibited as the diameter of body 120 varies between different sections of body 120 and also between each projection angle, such that each projection image exhibits a similar noise level. Determination of the tube current may also consider the generator/tube load and limits of system 110 to ensure appropriate tube capacity would be available throughout the subsequent CT scan.

According to some embodiments of S230, imaging parameter determination component 140 receives a user-specified reference image quality value. The reference image quality value is associated with reference tube current data specifying a tube current for various scanning z-positions and projection angles, assuming a "standard" patient attenuation profile. Next, the reference tube current data is modified based on the attenuation data determined by characteristics determination component 130 at S220. For example, the tube current is reduced at areas of the body that exhibit a smaller attenuation than that of corresponding areas of the standard patient, and is increased where the anatomy is more attenuating than corresponding anatomy of the standard patient. Generally, the tube current may be increased for larger patients (i.e., exhibiting greater-than-standard attenuation) and reduced for smaller patients (i.e., exhibiting less-than-standard attenuation).

Image quality is related to the ratio of signal (i.e., contrast, in the present example) to noise. The composition of a region may dictate the contrast level exhibited by a region for a given tube current. The tube current for each projection angle and patient z-position may therefore be further modified based on the determined composition at S230.

For example, the attenuation data may indicate that a larger patient requires a greater tube current than required by a smaller patient to image a region at a given image quality. However, if the composition of the region of the larger patient includes significant body fat, the tube current may be increased to a lesser degree than would have been determined in the absence of the composition data, due to the increased tissue contrast provided by fatty tissue. More specifically, fat exhibits a lower CT value than surrounding tissue and therefore results in higher contrast. Due to the increased contrast (in comparison to a body having less fat), a same signal-to-noise ratio may be achieved for a given large body size by using a smaller increase in tube current. Similarly, a smaller patient generally requires less tube current than an average-sized patient to achieve a similar image quality, but if it is determined that the smaller patient includes less fat and thereby provides lower tissue contrast than expected, the reduction in tube current determined at S230 may be of lesser magnitude than a case in which only attenuation was considered.

Figure 3:
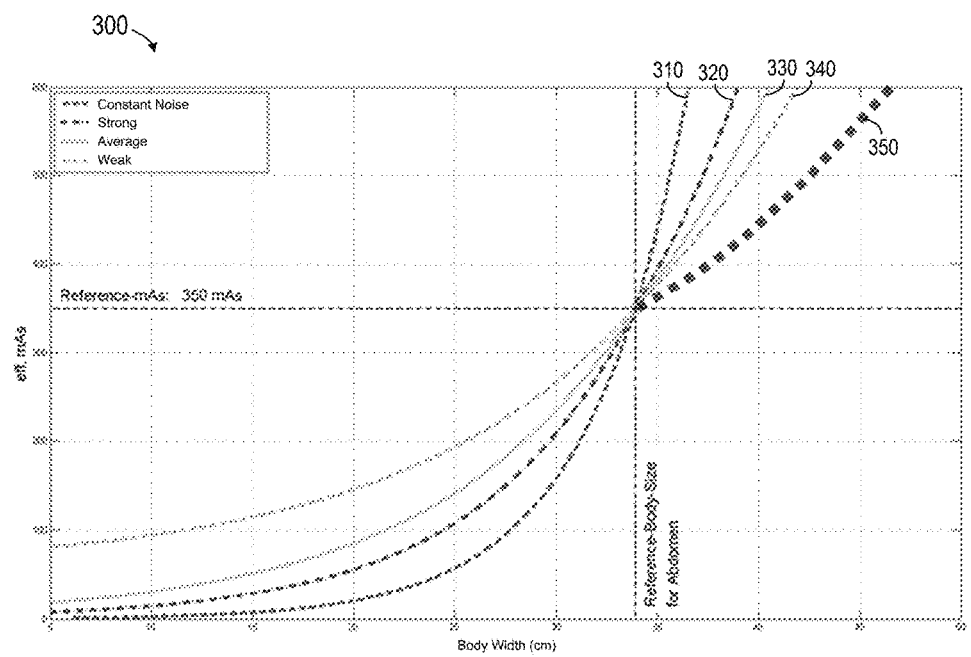
FIG. 3 illustrates determination of imaging parameters according to some embodiments.

FIG. 3 illustrates the determination of imaging parameters at S230 according to some embodiments. Graph 300 includes curves 310 through 340 for determining tube current for the abdominal region (i.e., patient z-positions corresponding to the abdominal area) based on attenuation. According to graph 300, body width is used as a proxy for attenuation.

Strong curve 320 represents larger tube current (or dose) modifications for a given change in attenuation than Average curve 330 and Weak curve 340. Constant Noise curve 310 reflects adaptations to the tube current which achieve constant image noise regardless of attenuation. From a clinical and technical perspective, more noise is often acceptable for imaging larger patients.

The determination of tube current may be based on curve 350 if the material composition of the abdominal area indicates an amount of fat above a given threshold. For body widths (i.e., attenuations) greater than the reference width, curve 350 indicates a lower tube current than any of curves 310 through 340. In other words, the determination of a threshold amount of fat results in the use of a more moderate tube current modulation curve than would otherwise be used at S230. Accordingly, curves 310 through 340 would be used to determine tube current for large body widths in which the amount of fat is less than a threshold, (e.g., a bodybuilder).

According to some embodiments, imaging parameter determination component 140 stores a reference tube current modulation curve (e.g., curve 320) associated with a projection. The reference tube current modulation curve is associated with a "standard" material composition at the projection. The actual composition of the body region to be imaged is determined as described above, and the reference tube current modulation curve is shifted to the left or to the right based on whether the composition provides more contrast (to the right) or less contrast (to the left) than the standard material composition. The shifted curve is then used to determine a tube current (y-axis) corresponding to the attenuation (or body width) at the projection (x-axis).

The imaging parameters determined at S230 may also include a tube voltage. Generally, lowering the tube voltage typically leads to an increase in contrast, thereby allowing for more noise while maintaining image quality. The extent of this increase is different for various materials such as, for example, iodine (high increase) and soft tissue (small increase). Therefore, simply reducing the tube voltage for a given tube current regardless of material composition or clinical indication (e.g., contrast-enhanced CT imaging) may reduce image quality due to increased noise, despite the increased contrast resulting from the reduced tube voltage.

Accordingly, in some embodiments, patient-specific mAs curves for producing the desired image quality are calculated for several tube voltages based on a given scan range, patient anatomy, and user-inputted contrast behavior (e.g., a CT scan type or tissue of interest). The curves may be shifted based on a determined material composition. Additionally or alternatively, the slope of a curve could be changed based on the material composition. Estimated doses are then calculated based on these curves for each tube voltage to determine the combination of tube voltage and tube current which provides the most-desirable dose efficiency.

Consequently, the intrinsic contrast (e.g., due to fat content) is considered along with the influence of the selected voltage on image contrast. In some embodiments, the spectral information of the topogram is used to detect and characterize-high attenuating objects with regard to their material characteristics. For example, in the case of titanium, the impact of the metal might be accounted for by increasing the dose through tube voltage and current adaptions so as to maintain the photon flow at the detector. In case of stainless steel metal implants (e.g., identified using spectral topogram data), increases in tube voltage and current would not significantly change the Signal-to-Noise ratio due to the attenuation exhibited by such implants. The metal might therefore be ignored during the determination of imaging parameters (i.e., tube current and tube voltage).

The target is imaged at S240 based on the determined imaging parameters. Imaging system 110 may be operated at S240 based on the imaging parameters to image body 120. In particular, imaging system 110 may acquire projection images of body 120 from many projection angles. Each projection image may be acquired using a tube current and tube voltage determined for its projection angle at S240. In a case that the projection images are acquired as body 120 moves with respect to imaging system 110 (e.g., through a gantry cavity), each projection image may be acquired using a tube current and tube voltage determined for its projection angle and patient z-position. A three-dimensional CT image of the target may be reconstructed based on the acquired projection images, which may be subsequently viewed on a slice-by-slice basis.

Some embodiments employ on-line attenuation-based tube current-modulation during imaging at S240. For example, during imaging, the attenuation used to determine the tube current for a given projection angle at S230 is compared against the actual attenuation measured 180 degrees earlier in the tube rotation. If the compared attenuations differ, the tube current determined for the given projection angle may be modified prior to acquiring a projection image at the given projection angle.

Figure 4:
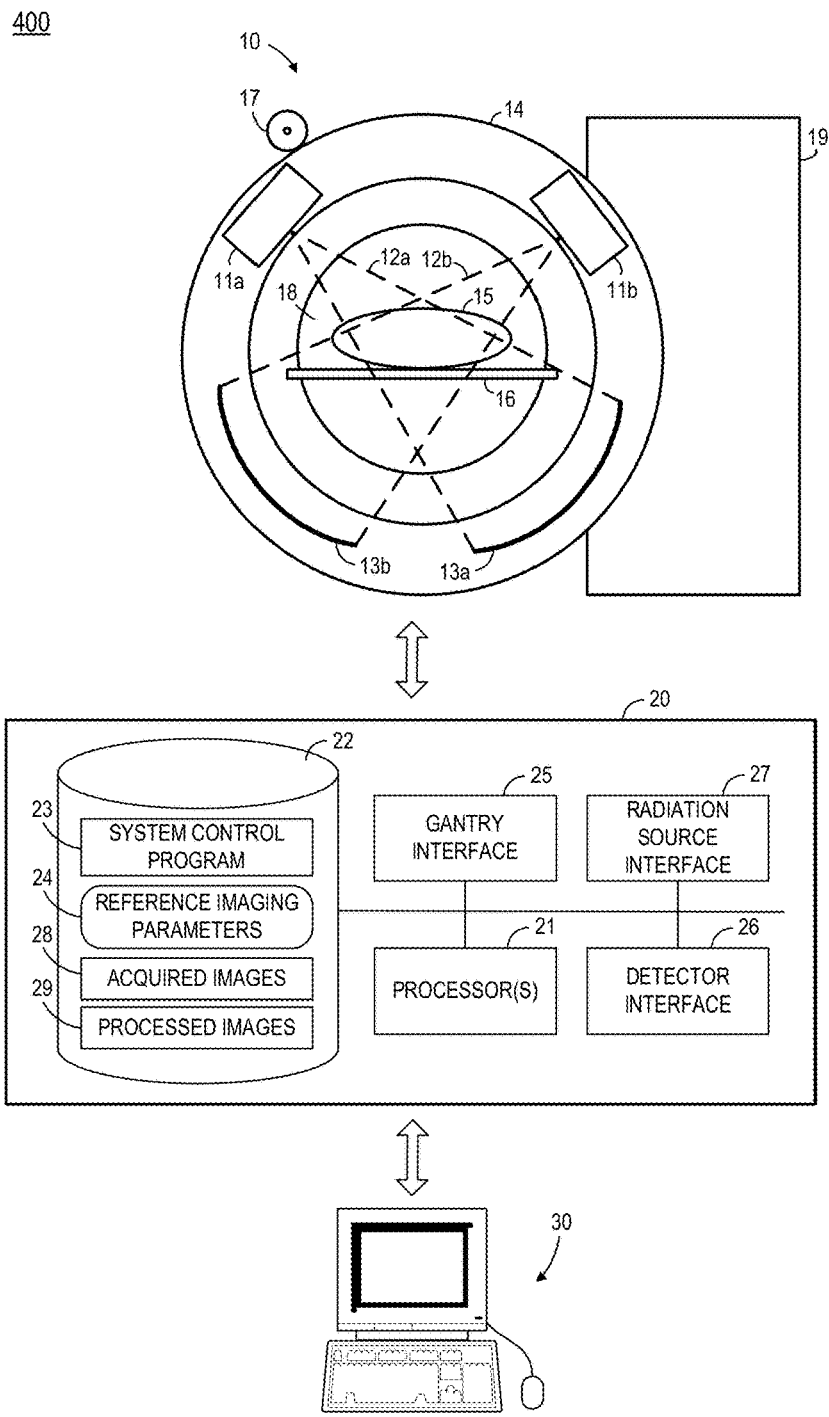
FIG. 4 illustrates an imaging system according to some embodiments.

FIG. 4 illustrates system 400 according to some embodiments. System 400 may comprise an implementation of system 100 of FIG. 1, but embodiments are not limited thereto. System 400 may also or alternatively operate to execute process 200 in some embodiments.

System 400 includes X-ray imaging system 10, control and processing system 20, and operator terminal 30. Generally, X-ray imaging system 10 acquires X-ray images of a patient volume. Control and processing system 20 controls X-ray imaging system 10 as described above to acquire the images and receives the acquired images therefrom. Control and processing system 20 processes the images and provides the processed images to terminal 30 for display thereby. Such processing may be based on user input received by terminal 30 and provided to control and processing system 20 by terminal 30.

Imaging system 10 comprises a CT scanner including X-ray sources 11a and 11b for emitting X-ray beams 12a and 12b toward opposing radiation detectors 13a and 13b. X-rays source 11a and 11b and radiation detectors 13a and 13b are mounted on gantry 14 such that they may be rotated through 360 degrees while maintaining the same physical relationship therebetween.

In operation, patient 15 is positioned on bed 16 to place a portion of patient 15 between X-ray sources 11a and 11b and their corresponding radiation detectors 13a and 13b. Next, X-ray sources 11a and 11b and their radiation detectors 13a and 13b are rotated by rotation drive 17 around cavity 18 in which patient 15 lies. During this rotation, X-ray sources 11a and 11b are powered by high-voltage generator 19 to transmit X-ray radiation toward detectors 13a and 13b. Detectors 13a and 13b each receive the radiation and produce a set of data (i.e., a raw image) for each projection angle. Embodiments are not limited to CT scanners.

X-ray sources 11a and 11b may comprise any suitable radiation source. In some embodiments, X-ray sources 11a and 11b emit electron, photon or other type of radiation having different ranges of energies. According to some embodiments, X-ray sources 11a and 11b are tubes with rotating anodes exhibiting polychromatic spectra consisting of a continuous spectrum of bremsstrahlung superimposed with characteristic lines of the tungsten material of the anode. According to some embodiments, X-ray sources 11a and 11b may be operated at different energies during the acquisition of a spectral topogram as described above.

Radiation detectors 13a and 13b may comprise any system to acquire an image based on received X-ray radiation. In some embodiments, radiation detectors 13a and 13b use a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge. In other embodiments, one or both of radiation detectors 13a and 13b convert received photons to electrical charge without requiring a scintillator layer. The photons are absorbed directly by an array of amorphous selenium photoconductors. The photoconductors convert the photons directly to stored electrical charge.

The charge detected by detectors 13a and 13b represents radiation intensities at each location of radiation fields produced by X-rays emitted from radiation sources 11a and 11b, respectively. The radiation intensity at a particular location of each radiation field represents the attenuative properties of materials lying along a divergent line between detectors 13a and 13b and the particular location of the radiation field. The set of radiation intensities acquired by each radiation detector 13a and 13b therefore represents a two-dimensional projection image of these materials. In some embodiments, several 2D projection images are acquired (i.e., Multidetector CT).

System 20 may comprise any general-purpose or dedicated computing system. Accordingly, system 20 includes one or more processors 21 configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of system control program 23. The program code of system control program 23 may be executable by one or more processors 21 to control imaging system 10 to acquire a spectral topogram of body 15, to determine characteristics of body 15 including material composition of body 15 based on the spectral topogram, to determine imaging parameters based on the characteristics, and to control imaging system 10 to acquire an image of body 15 based on the imaging parameters. In this regard, storage device 22 also includes reference imaging parameters 24 which may be modified as described above to determine the imaging parameters. System 20 includes gantry interface 25, detector interface 26 and radiation source interface 27 for controlling corresponding elements of imaging system 10 to acquire images.

Images acquired by system 10 (e.g., topogram projections and CT image projections) are stored in data storage device 22 as acquired images 28, in DICOM or another data format. Each acquired image 28 may be further associated with details of its acquisition, including but not limited to imaging plane position and angle, imaging position, radiation source-to-detector distance, patient anatomy imaged, patient position, X-ray tube current, X-ray tube voltage, image resolution and radiation dosage.

Processor(s) 21 may execute system control program 23 to process acquired images 28, resulting in processed images 29. Processing may include generation of three-dimensional CT images from acquired projection images. Processed images 29 may be provided to terminal 30, and system 20 may also receive input from terminal 30, which may be used to control image acquisition and/or processing of acquired images 28.

Terminal 30 may comprise a display device and an input device coupled to system 20. In some embodiments, terminal 30 is a separate computing device such as, but not limited to, a desktop computer, a laptop computer, a tablet computer, and a smartphone. Terminal 30 displays processed images 29 received from system 20 and receives user input for controlling system 10.

Each of system 10, system 20 and terminal 30 may include other elements which are necessary for the operation thereof, as well as additional elements for providing functions other than those described herein.

According to the illustrated embodiment, system 20 controls the elements of system 10. System 20 also processes images received from system 10. Moreover, system 20 receives input from terminal 30 and provides processed images to terminal 30. Embodiments are not limited to a single system performing each of these functions. For example, system 10 may be controlled by a dedicated control system, with the acquired images being provided to a separate image processing system over a computer network or via a physical storage medium (e.g., a DVD).

Figure 5:
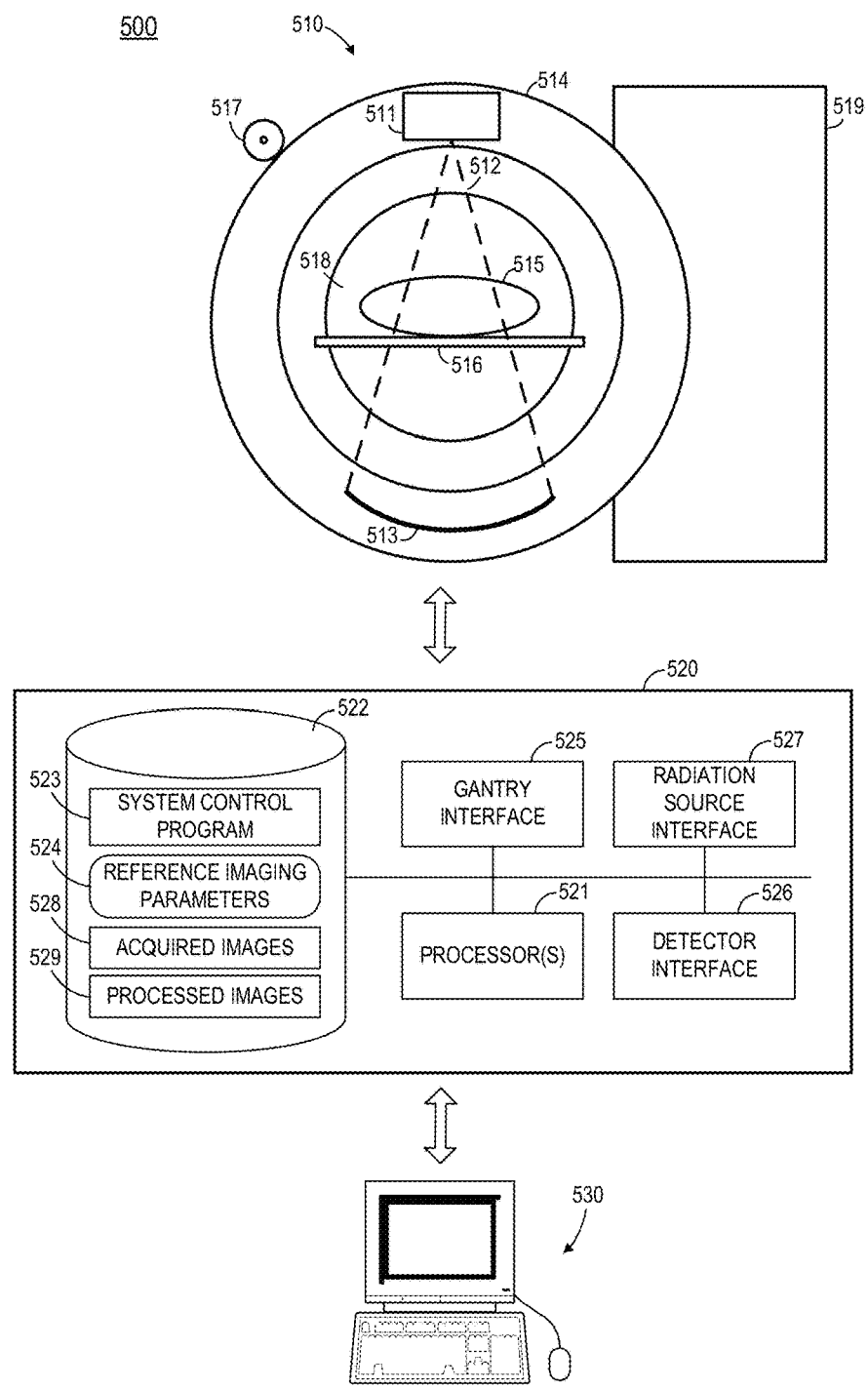
FIG. 5 illustrates an imaging system according to some embodiments.

FIG. 5 illustrates system 500 according to some embodiments. Imaging device 510 includes single X-ray source 511 and detector 513. According to some embodiments, projection images are acquired using different photon energy levels by switching the voltage of X-ray source and reading out the projection data from detector 513 at time points corresponding to each different energy level. In other embodiments, a split filter (e.g., Au and Sn) results in a low-energy half and a high-energy half of beam 512 incident on patient 515.

In some embodiments, detector 513 is capable of acquiring spectral information in order to generate multiple images, each of which corresponds to a different range of photon energies based on a single broad-spectrum radiation emission from source 511. Such a detector 513 may comprise a two-layer or "sandwich" detector with each layer possessing different spectral sensitivities.

In some embodiments, detector 513 is a photon counting detector. Cnventional detectors measure energy-integrated signals of all received X-ray photons and therefore discard all energy-dependent information. In contrast, photon counting detectors provide energy-specific information relating to received radiation. For example, some known photon counting detectors use pulse-height analysis to record the number of photons of the received energy spectrum that lie within each of specified energy windows.

As described with respect to FIG. 4, patient 515 or another volume is positioned on bed 516 to place a portion of interest of between X-ray source 511 and radiation detector 513. X-ray source 111 is controlled to transmit a spectrum of X-ray radiation toward detector 513 as gantry 514 is rotated around cavity 518. Detector 513 receives the radiation and produces a set of data (i.e., a projection image) for each specified photon energy and at each desired projection angle.

More particularly, an energy image may be created for each of several different energy ranges. For example, assuming that detector 513 is a photon counting detector, detector 513 receives the radiation that has passed though body 515 and produces one energy image representing the photons above 25 keV, one energy image representing the photons above 75 keV, and one energy image representing the photons above 85 keV at each pixel location. Each energy image therefore represents attenuative properties of portions of body 515 at a specific photon energy range. This spectral information may be used to determine the composition of the portions of body 515 depicted in the images.

The remaining components of system 500 may otherwise operate as described above with respect to similarly-named components of system 400.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A system comprising:
    an imaging system comprising an X-ray source and an X-ray detector, the imaging system to acquire a spectral topogram of a target; and
    a processor to execute program code to:
        determine, based on the spectral topogram, an attenuation associated with each of a plurality of regions of the target and a composition of each of the plurality of regions;
        determine imaging parameters associated with the plurality of regions based on the determined attenuation and composition; and
        transmit the determined imaging parameters to the imaging system,
    wherein the imaging system is to acquire an image of the target based on the transmitted imaging parameters.

2. A system according to claim 1, wherein determination of imaging parameters associated with the plurality of regions comprises:
    determination of a first tube current associated with a first region of the target based on an attenuation associated with the first region and a composition of the first region.

3. A system according to claim 2, wherein determination of the first tube current comprises determination of an intermediate tube current based on the attenuation associated with the first region and modification of the intermediate tube current based on the composition of the first region.

4. A system according to claim 3, wherein determination of the intermediate tube current comprises modifying a reference tube current based on the attenuation associated with the first region, wherein the reference tube current is associated with a reference attenuation.

5. A system according to claim 2, wherein determination of imaging parameters associated with the plurality of regions comprises:
    determination of a second tube current associated with a second region of the target based on an attenuation associated with the second region and a composition of the second region.

6. A system according to claim 5, wherein the attenuation associated with the first region is similar to the attenuation associated with the second region, wherein the composition of the first region includes more fat than the composition of the second region, and wherein the first tube current is lower than the second tube current.

7. A system according to claim 5, wherein the attenuation associated with the first region is greater than the attenuation associated with the second region, wherein the composition of the first region includes more fat than the composition of the second region, and wherein the first tube current is lower than the second tube current.

8. A method comprising:
    acquiring a spectral topogram of a target;
    determining, based on the spectral topogram, an attenuation associated with each of a plurality of regions of the target and a composition of each of the plurality of regions;
    determining imaging parameters associated with the plurality of regions based on the determined attenuation and composition; and
    acquiring an image of the target based on the imaging parameters.

9. A method according to claim 8, wherein determining imaging parameters associated with the plurality of regions comprises:
    determining a first tube current associated with a first region of the target based on an attenuation associated with the first region and a composition of the first region.

10. A method according to claim 9, wherein determining the first tube current comprises determining an intermediate tube current based on the attenuation associated with the first region and modification of the intermediate tube current based on the composition of the first region.

11. A method according to claim 10, wherein determining the intermediate tube current comprises modifying a reference tube current based on the attenuation associated with the first region, wherein the reference tube current is associated with a reference attenuation.

12. A method according to claim 9, wherein determining imaging parameters associated with the plurality of regions comprises:
    determining a second tube current associated with a second region of the target based on an attenuation associated with the second region and a composition of the second region.

13. A method according to claim 12, wherein the attenuation associated with the first region is similar to the attenuation associated with the second region, wherein the composition of the first region includes more fat than the composition of the second region, and wherein the first tube current is lower than the second tube current.

14. A method according to claim 12, wherein the attenuation associated with the first region is greater than the attenuation associated with the second region, wherein the composition of the first region includes more fat than the composition of the second region, and wherein the first tube current is lower than the second tube current.

15. A system comprising:
    an interface to acquire a spectral topogram of a target; and
    a processor to execute program code to:
        determine, based on the spectral topogram, an attenuation associated with each of a plurality of regions of the target and a composition of each of the plurality of regions;
        determine imaging parameters associated with the plurality of regions based on the determined attenuation and composition; and
        transmit the determined imaging parameters to an imaging system.

16. A system according to claim 15, wherein determination of imaging parameters associated with the plurality of regions comprises:
    determination of a first tube current associated with a first region of the target based on an attenuation associated with the first region and a composition of the first region.

17. A system according to claim 16, wherein determination of the first tube current comprises determination of an intermediate tube current based on the attenuation associated with the first region and modification of the intermediate tube current based on the composition of the first region.

18. A system according to claim 17, wherein determination of the intermediate tube current comprises modifying a reference tube current based on the attenuation associated with the first region, wherein the reference tube current is associated with a reference attenuation.

19. A system according to claim 16, wherein determination of imaging parameters associated with the plurality of regions comprises:
   determination of a second tube current associated with a second region of the target based on an attenuation associated with the second region and a composition of the second region.

20. A system according to claim 19, wherein the attenuation associated with the first region is similar to the attenuation associated with the second region, wherein the composition of the first region includes more fat than the composition of the second region, and wherein the first tube current is lower than the second tube current.

* * * * *